(12) United States Patent
Amariglio et al.

(10) Patent No.: US 11,369,373 B2
(45) Date of Patent: Jun. 28, 2022

(54) SURGICAL STAPLER

(71) Applicant: Lexington Medical, Inc., Billerica, MA (US)

(72) Inventors: Leon Amariglio, Lexington, MA (US); Andrew Marecki, West Boylston, MA (US)

(73) Assignee: Lexington Medical, Inc., Bedford, MA (US)

( * ) Notice: Subject to any disclaimer, the term of this patent is extended or adjusted under 35 U.S.C. 154(b) by 0 days.

(21) Appl. No.: 16/750,367

(22) Filed: Jan. 23, 2020

(65) Prior Publication Data
US 2020/0229814 A1 Jul. 23, 2020

Related U.S. Application Data

(60) Provisional application No. 62/795,609, filed on Jan. 23, 2019.

(51) Int. Cl.
*A61B 17/072* (2006.01)

(52) U.S. Cl.
CPC .. *A61B 17/072* (2013.01); *A61B 2017/07228* (2013.01); *A61B 2017/07257* (2013.01); *A61B 2017/07271* (2013.01)

(58) Field of Classification Search
CPC .............. A61B 17/072; A61B 17/068; A61B 17/07207; A61B 17/105; A61B 17/115; A61B 17/1155; A61B 2017/1157; A61B 2017/07228; A61B 2017/07257; A61B 2017/07271; A61B 2017/07221; A61B 2017/07264
See application file for complete search history.

(56) References Cited

U.S. PATENT DOCUMENTS

| | | |
|---|---|---|
| 5,474,223 A | 12/1995 | Viola et al. |
| 5,522,534 A | 6/1996 | Viola et al. |
| 5,588,579 A | 12/1996 | Schnut et al. |
| 5,758,814 A | 6/1998 | Gallagher et al. |
| 5,799,857 A | 9/1998 | Robertson et al. |
| 5,836,503 A | 11/1998 | Ehrenfels et al. |
| 6,945,444 B2 | 9/2005 | Gresham et al. |

(Continued)

FOREIGN PATENT DOCUMENTS

| CN | 202982106 U | * | 6/2013 | ........... A61B 17/072 |
| WO | WO-8300614 A1 | * | 3/1983 | ........... A61B 17/072 |

(Continued)

OTHER PUBLICATIONS

NL 2021816 (priority document of PCT/NL2019/050678), filed Oct. 15, 2018 (Year: 2018).*

*Primary Examiner* — Stephen F. Gerrity
*Assistant Examiner* — Linda J Hodge
(74) *Attorney, Agent, or Firm* — Brooks, Cameron & Huebsch, PLLC

(57) ABSTRACT

The present disclosure includes apparatuses for a surgical stapler. An example surgical stapler can include a handle assembly and a body portion extending from the handle portion, the body portion having a staple cartridge assembly, the staple cartridge assembly defining a first row of staple receiving slots, the staple receiving slots have an outer edge, wherein the staple receiving slots are arranged in a generally radial orientation with respect to the center axis of the staple cartridge assembly.

7 Claims, 4 Drawing Sheets

(56) References Cited

U.S. PATENT DOCUMENTS

| | | |
|---|---|---|
| 6,957,758 B2 | 10/2005 | Aranyi |
| 7,168,604 B2 | 1/2007 | Milliman et al. |
| 7,234,624 B2 | 6/2007 | Gresham et al. |
| 7,303,106 B2 | 12/2007 | Milliman et al. |
| 7,325,713 B2 | 2/2008 | Aranyi |
| 7,364,060 B2 | 4/2008 | Milliman |
| 7,398,907 B2 | 7/2008 | Racenet et al. |
| 7,494,038 B2 | 2/2009 | Milliman |
| 7,516,877 B2 | 4/2009 | Aranyi |
| 7,546,940 B2 | 6/2009 | Milliman et al. |
| 7,611,038 B2 | 11/2009 | Racenet et al. |
| 7,802,712 B2 | 9/2010 | Milliman et al. |
| 7,824,426 B2 | 11/2010 | Racenet et al. |
| 7,857,187 B2 | 12/2010 | Milliman |
| 7,926,692 B2 | 4/2011 | Racenet et al. |
| 8,123,101 B2 | 2/2012 | Racenet et al. |
| 8,136,712 B2 | 3/2012 | Zingman |
| 8,141,763 B2 | 3/2012 | Milliman |
| 8,360,296 B2 | 1/2013 | Zingman |
| 8,684,249 B2 | 4/2014 | Racenet et al. |
| 8,910,847 B2 | 12/2014 | Nalagatla et al. |
| 2016/0089146 A1* | 3/2016 | Harris .............. A61B 17/072 227/179.1 |
| 2017/0281155 A1* | 10/2017 | Shelton, IV ........ A61B 17/105 |
| 2018/0289370 A1 | 10/2018 | Amariglio et al. |
| 2018/0368832 A1 | 12/2018 | Marecki et al. |

FOREIGN PATENT DOCUMENTS

| | | | | |
|---|---|---|---|---|
| WO | WO-2015032797 A1 * | 3/2015 | ......... | A61B 17/1155 |
| WO | WO-2020080937 A2 * | 4/2020 | ......... | A61B 17/1155 |

* cited by examiner

SURGICAL STAPLER

PRIORITY INFORMATION

This application claims benefit of U.S. Provisional Application No. 62/795,609 filed Jan. 23, 2019, the specification of which is incorporated herein by reference.

TECHNICAL FIELD

The present disclosure relates generally to a surgical stapling instrument.

BACKGROUND

Anastomosis is the surgical joining of separate hollow lumen or organ sections to allow the sections to communicate with each other. An anastomosis can follow a procedure in which a section of hollow tissue is removed, such as a section of the intestine, and the remaining end sections are to be joined. Depending on the desired anastomosis procedure, the end sections may be joined end-to-end or side-to-side, for example.

Circular surgical stapler instruments that perform an anastomosis procedure are known. The instrument joins two ends of the organ sections by driving a circular array of staples through the organ sections and cutting the tissue to form a tubular passage. The instrument includes an actuating handle assembly and a tubular body portion extending therefrom. The body portion receives a staple cartridge assembly and has a shaft that connects to an anvil assembly. The staples are arranged along a circle of the staple cartridge. Retraction of the shaft clamps tissue between the anvil assembly and the staple cartridge assembly. Staples are driven into staple receiving recesses and the tissue is cut by a circular knife.

After the staples have been fired, the entire instrument must be removed from the site. The anvil assembly has a rigid anvil head and has a profile that can make it difficult to remove the instrument from the tubular organ. In order to reduce the transverse profile of the anvil assembly during placement and removal of the anvil assembly from a hollow organ, anvil assemblies having a tiltable anvil head have been developed. The pivotable anvil head is normally locked in the operative firing position. Upon firing the stapling device, the lock is released and the anvil head moves to a position that is tilted with respect to the shaft.

While known staplers provide physicians with a tool for creating an anastomosis, a need still exists for an improved surgical stapling instrument that minimizes clinical problems associated with prior devices.

DETAILED DESCRIPTION

Figure 1:
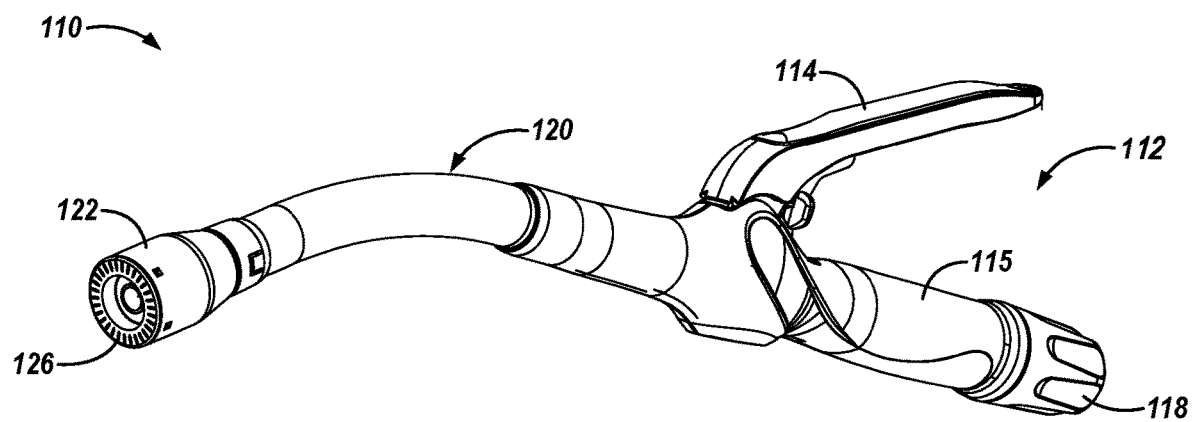
FIG. 1 is a perspective view of a surgical stapling instrument in accordance with an embodiment of the present disclosure, without an anvil head.

The present disclosure includes apparatuses for a surgical stapler. An example surgical stapler can include a handle assembly and a body portion extending from the handle portion, the body portion having a staple cartridge assembly, the staple cartridge assembly defining a first group (e.g., row) of staple receiving slots, the staple receiving slots have an outer edge, wherein the staple receiving slots are arranged in a generally radial orientation with respect to the center axis of the staple cartridge assembly.

Circular staplers are used by physicians in a number of areas. Circular staplers can be used to repair rectal prolapse and hemorrhoid disease, in bowel resections where a diseased part of the large intestine is removed, and for esophagogastric disease. Circular staplers can be used for end-to-end anastomosis as well as for side-to-end and side-to-side anastomoses. Prior art staplers have one or two rows of staplers where the staples are arranged along a circle that runs around the longitudinal axis of a staple cartridge assembly.

In an effort to achieve satisfactory outcomes, physicians must consider compression, staple height, tissue thickness, tissue compressibility, and tissue type prior to choosing a stapler and cartridge. However, in some instances even where the physician chooses the proper staple and cartridge, less than optimal results can show up weeks or months after the procedure. In these instances, it is noted that the tissue on the inside of the joined lumens has necrosis which can lead to staple ring failure. In some instances, the tissue will dry up and flake away from the staples. Applicants believe that poor blood perfusion to this area is a contributing factor.

In an effort to improve long term clinical outcomes, a circular stapler is described wherein the staples are arranged in a radial, or nearly radial fashion, such that a largest dimension of the staples are oriented toward a center axis of a staple cartridge assembly. In addition to allowing improved blood perfusion, more staples, as compared to one or two circles of staples, can be used which results in improved hold strength.

According to an aspect of the present disclosure, a surgical stapling instrument, comprising a handle assembly a body portion extending from the handle assembly, and an anvil assembly is disclosed. The body portion can include a rod and a staple cartridge assembly. The staple cartridge assembly defines staple receiving slots such that the staples are arranged in a radial fashion. The anvil assembly includes an anvil head, an anvil member, an anvil shaft, and optionally a biasing member. The anvil shaft defines a longitudinal axis and is connectable to the rod. The anvil member may be pivotally secured to the anvil head about a transverse axis, the transverse axis being transverse to the longitudinal axis. The anvil member defines staple forming recesses. The biasing member is supported on the anvil assembly to urge the anvil member from a first position to a second position defining an angle with respect to the longitudinal axis.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "X", "Y", "N", "M", etc., particularly with respect to reference numerals in the drawings, indicate that a number of the particular feature so designated can be included. It is also to be understood that the terminology used herein is for the purpose of describing particular embodiments only, and is not intended to be limiting. As used herein, the singular forms "a", "an", and "the" can include both singular and plural referents, unless the context clearly dictates otherwise. In addition, "a number of", "at least one", and "one or more" (e.g., a number of pivot points) can refer to one or more pivot points, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 126 may reference element "26" in FIG. 1, and a similar element may be referenced as 226 in FIG. 2. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

Preferred embodiments of the presently disclosed instrument will now be described in detail with reference to the drawings in which like reference numerals designate identical or corresponding elements in each of the several views. The term "proximal," as is customary, refers to a position closer to the surgeon or user, whereas the term "distal" refers to a position farther away from the surgeon or user.

FIG. 1 illustrates a circular surgical stapling instrument 110, without the anvil attached. Surgical stapling instrument 110 includes a handle assembly 112 having at least one pivotable actuating handle 114, stationary handle 115 and a rotatable actuator 118. A tubular body portion 120 extends from the handle assembly 112. The tubular body portion 120, which generally has a circular cross-sectional shape, may have a straight or a curved shape along its length and may be flexible or relatively rigid. Cross-sectional shapes other that circular are contemplated, so that the tubular body portion 120 can have a polygonal, elliptical, semi-circular, ovoid, or other shape. The body portion 120 terminates in a staple cartridge assembly 122 which includes a distally facing tissue contacting surface 126. The longitudinal axis of the body portion 120 can located along an axis that travels proximally to distally in the body portion 120. A center axis of the body portion 120 can be located at the center of the body portion 120.

Figure 2:
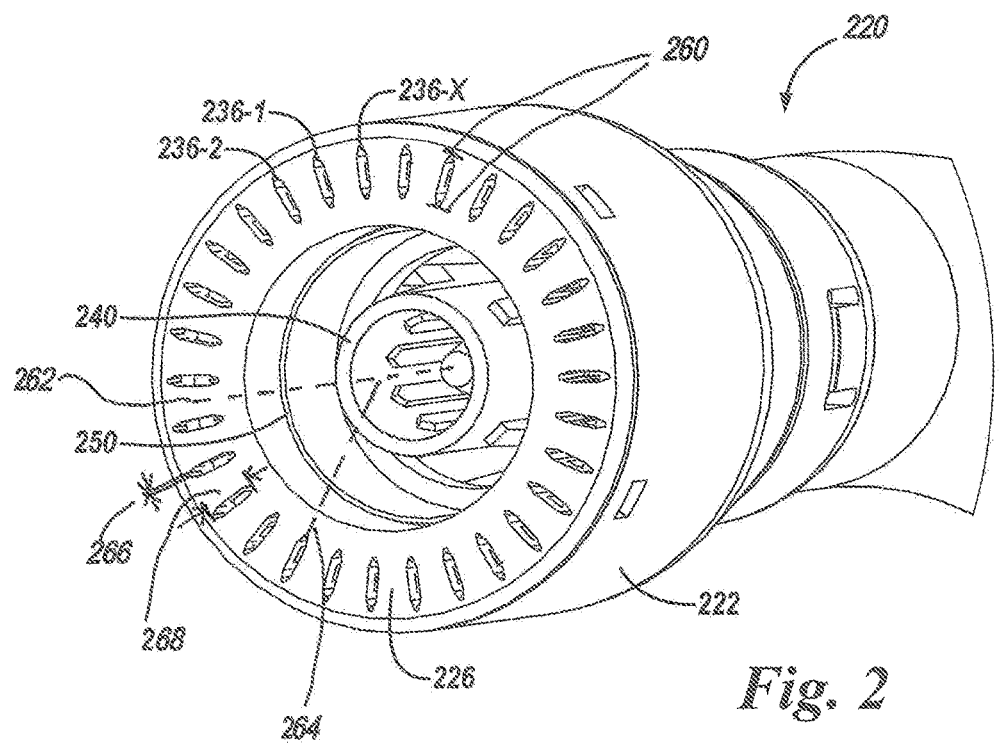
FIG. 2 is a perspective view of the distal end of a surgical stapling instrument in accordance with an embodiment of the present disclosure, without an anvil head.

FIG. 2 illustrates the distal end of a stapling instrument. Staple cartridge assembly 222 which includes a distally facing tissue contacting surface 226 having a row of radially directed staple receiving slots 236-1, 236-2, 236-X. The staple receiving slots 236-1, 236-2, 236-X can be oriented in a general radial configuration such that a largest 268 dimension of the staple receiving slots are at an angle between 0° and 45° to a radial line 264 from the center axis 262 of the staple cartridge assembly to an outer edge 260 of the staple receiving slots. Stated in another way, a smallest dimension 266 of the first row of staple receiving slots faces substantially toward a center axis 262 of the staple cartridge assembly, such that a line perpendicular to the outer edge of the staple receiving slots forming the smallest dimension of the staple receiving slots would be directed toward the center axis 262 of the staple cartridge assembly. Each staple receiving slot has a staple (not shown) disposed therein. As will be shown later, an anvil assembly is positioned distally of the staple cartridge assembly 222, which includes an anvil member and an anvil shaft operatively associated therewith. The anvil assembly has a proximally facing tissue contacting surface that defines staple forming recesses that correspond to the row of staple receiving slots. The tubular body portion 220 has a rod or shaft 240 centrally located with respect to the staple cartridge assembly 222, with an anvil retainer assembly on the distal end. The shaft of the anvil assembly is removably connectable to the rod or shaft 240 of the tubular body portion 220. Also shown is tissue cutter 250.

Figure 3:
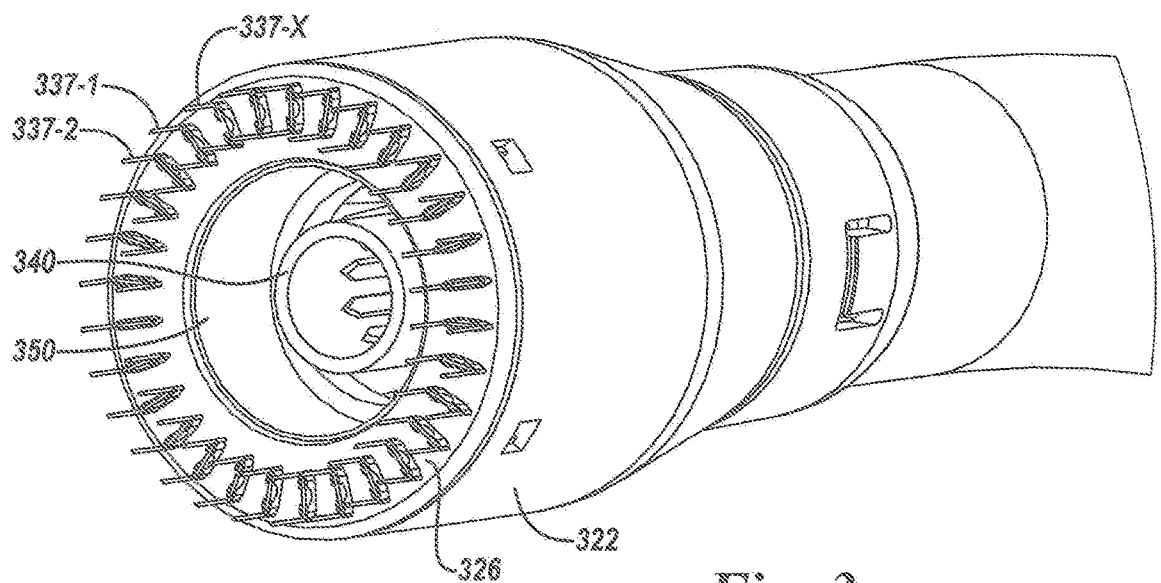
FIG. 3 is a perspective view of the distal end of a surgical stapling instrument in accordance with an embodiment of the present disclosure, without an anvil head but with staples.

FIG. 3, which is similar to FIG. 2, shows the staples 337-1, 337-2, 337-X extending from the staple slots 336. The cutter (e.g., knife) 350 is also shown in an advanced state. As will be described later, movement of moveable handle (e.g., 114 in FIG. 1) toward the stationary handle portion (e.g., 115 in FIG. 1) causes the rod or shaft 340 to advance a staple pusher and the tissue cutter 350.

Figure 4:
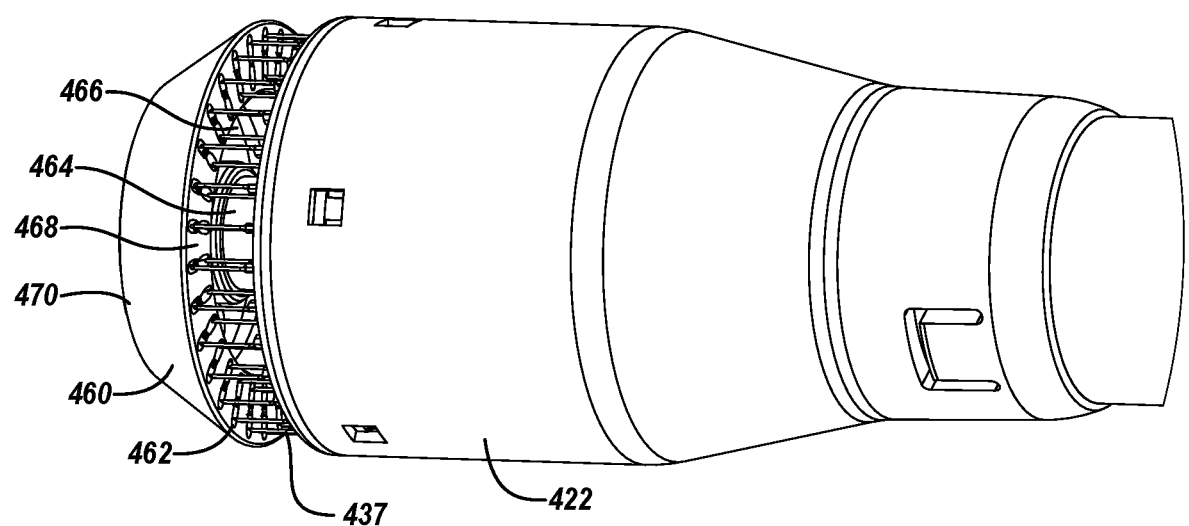
FIG. 4 is a perspective view of the distal end of a surgical stapling instrument in accordance with an embodiment of the present disclosure with the staples nearly deployed.

FIG. 4 illustrates the staple cartridge assembly 422 with anvil assembly 460. Anvil assembly 460 includes proximal facing tissue contacting surface 468. Positioned on the proximal facing surface 468 are a plurality of pockets 462 for receiving and deforming staples 437 as they are delivered. Anvil assembly 460 also includes anvil head assembly 470 and an anvil rod assembly 464. Anvil head assembly 470 includes a backup plate (not shown) and a cutting ring 466. Although not shown, the anvil head assembly 470 can be tilt-able relative to the stapler body. At the proximal end, anvil rod assembly 464 interfaces with the anvil receiving portion of rod or shaft (rod or shaft 240 in FIG. 2).

Staple cartridge assembly (e.g., 122 in FIG. 1, 222 in FIG. 2, 322 in FIG. 3, 422 in FIG. 4) can include a staple pusher (not shown) with a distal portion defining a ring of peripherally spaced fingers (not shown), each one of which is received within a respective staple receiving slot. A knife (e.g., 250 in FIG. 2, 350 in FIG. 3) having a cutting edge is disposed within the staple cartridge assembly (e.g., 122 in FIG. 1, 222 in FIG. 2, 322 in FIG. 3, 422 in FIG. 4). The knife edge is circular and disposed radially inward of the rows of staples. The knife (e.g., 250 in FIG. 2, 350 in FIG. 3) is mounted so that as the staple pusher is advanced axially in the direction of the anvil assembly, the knife (e.g., 250 in FIG. 2, 350 in FIG. 3) is also advanced axially. The staple pusher is advanced in the distal direction to drive staples from the staple receiving slots 36 against the anvil member so that the staple forming recesses (e.g., 462 in FIG. 4) form the staples in a closed shape. As the pusher (e.g., rod or shaft 240 in FIG. 2, 340 in FIG. 3) is advanced, the knife (e.g., 250 in FIG. 2, 350 in FIG. 3) is advanced and driven toward the anvil assembly (e.g., 470 in FIG. 4) to cut tissue. When the staples are fully deployed, the knife (e.g., 250 in FIG. 2, 350 in FIG. 3) is pressed against cutting ring (e.g., 466 in FIG. 4) to effect the cutting of tissue so that the lumen or organ is open.

Other aspects of the stapler are as known in the art. Rotatable actuator is used to move the anvil assembly closer to or away from the staple cartridge assembly. The device (e.g., 110 in FIG. 1) can include a mechanism that shows the user how far apart the proximal face (e.g., 468 in FIG. 4) is from the distal face (e.g., 126 in FIG. 1, 226 in FIG. 2, 326 in FIG. 3). When ready to deploy the staples, the stapler may have a safety mechanism that will prevent staples from being delivered before the user/physician is ready for the delivery. When moveable handle (e.g., 114 in FIG. 1) is advanced toward handle (e.g., 115 in FIG. 1), the staples are forced from the cartridge assembly (e.g., 122 in FIG. 1, 222 in FIG. 2, 322 in FIG. 3, 422 in FIG. 4) toward the anvil assembly (e.g., 460 in FIG. 4) wherein the closed shape of the staples is formed.

Staples of any size, shape, or cross section, as is known in the art, can be used with this invention. The figures show a single row of radial staples. In some embodiments, more than one row of radially facing staples can be used. In some embodiments, the staples can be offset from one another in a radial direction, in a staggered fashion. For example, the end of one staple may be lined up with the center of an adjacent staple. In some embodiments, the staples may not be in a true radial orientation. In some embodiments, circumferential rows of staples (one or more) may be used with the row of radial staples.

Figure 5A:
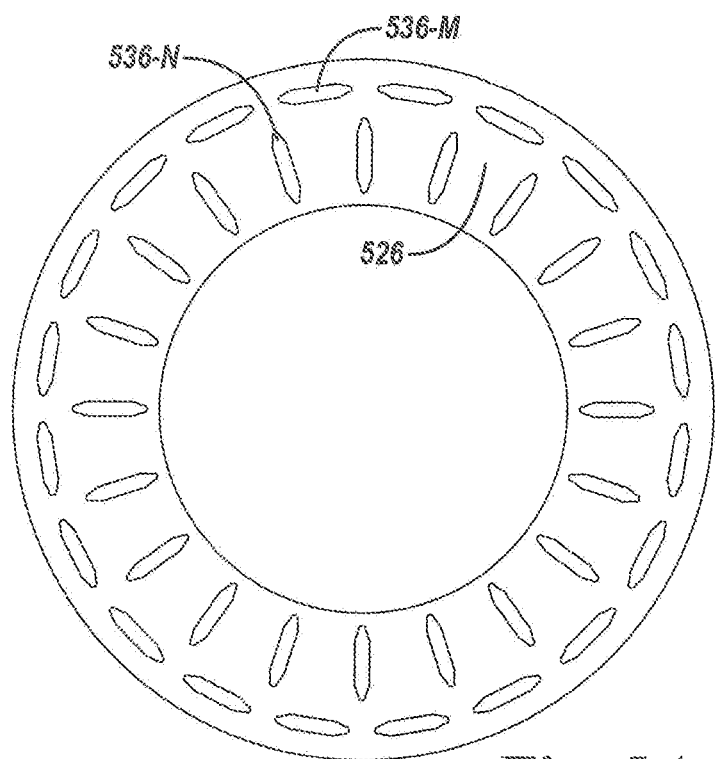
FIGS. 5A and 5B are schematics showing alternative staple arrangements.
Figure 5B:
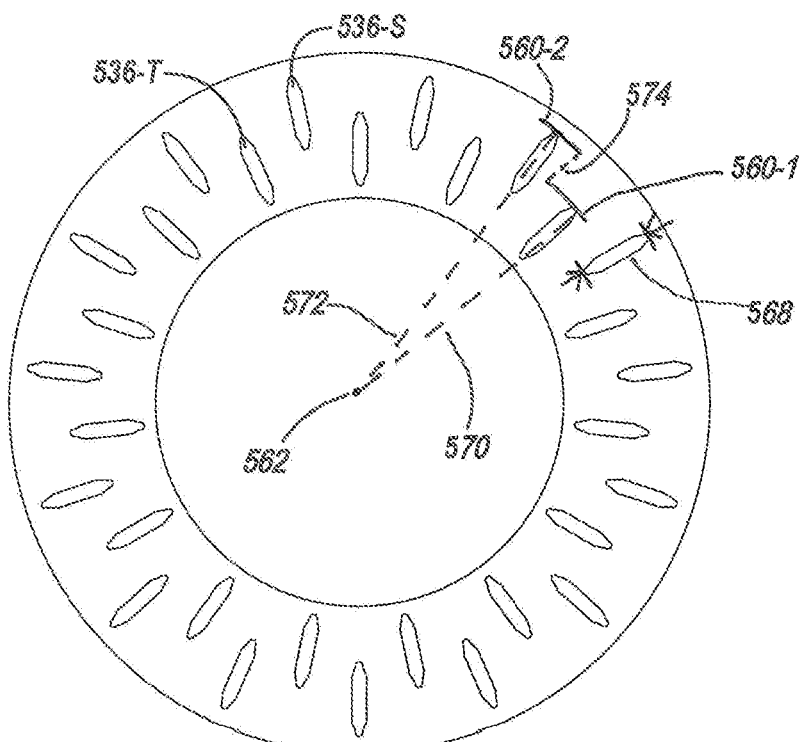

FIGS. 5A and 5B are schematics showing alternative staple arrangements. FIGS. 5A and 5B show two alternate arrangements of the staples as viewed from the distal facing face 526 (e.g., 126 in FIG. 1, 226 in FIG. 2, 326 in FIG. 3). In FIG. 5A, staple receiving slots 536-M (with a staple (not shown) disposed therein) is circumferentially oriented and staple receiving slots 536-N (with a staple (not shown) disposed therein) are radially oriented. In FIG. 5B, there are two rows of staggered radially oriented staple receiving slots, 536-T and 536-S (each with a staple (not shown) disposed therein). The outer edge 560-1 of staple receiving slot row 536-T can be located a first distance 570 from the center axis 562 of the staple cartridge assembly and the outer edge 560-2 of the staple receiving slot row 536-S can be located a second distance 572 from the center axis 562 of the staple cartridge assembly, where a difference 574 between the first distance 570 and the second distance 572 is less than a largest dimension 568 of the each of the staple receiving slots. In a number of embodiments, the distal facing face can include any number of row of staple receiving slots. For example, the distal facing face can include 2 rows of radial oriented staple receiving slots and 1 row of circumferentially oriented staple receiving slots. The anvil assembly can include pockets that match staple receiving slots of the staple cartridge assembly to receive staples from the staple cartridge assembly.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A surgical stapler, comprising:
a handle assembly; and
a body portion extending from the handle portion, the body portion having a staple cartridge assembly, the staple cartridge assembly defining a first row of staple receiving slots and a second row of staple receiving slots, wherein each of the staple receiving slots have an outer edge comprising a smallest dimension of the staple receiving slots;
wherein the outer edge of each staple receiving slot of the first row of staple receiving slots are a first distance from a center axis of the staple cartridge assembly;
wherein the outer edge of each staple receiving slot of the second row of staple receiving slots are a second distance, different from the first distance, from the center axis of the staple cartridge assembly;
wherein a difference between the first distance and the second distance is less than a largest dimension of the each of the staple receiving slots; and
wherein the staple receiving slots are arranged in a generally radial orientation with respect to the center axis of the staple cartridge assembly such that the largest dimension of each of the staple receiving slots is along a radial line from the center axis of the staple cartridge assembly.

2. The surgical stapler of claim 1, further comprising an anvil member, the anvil member defining staple forming recesses.

3. The surgical stapler of claim 1, wherein the outer edges of the staple receiving slots are arranged in a staggered fashion such that the staple receiving slots of the first row are adjacent to the staple receiving slots of the second row.

4. A staple cartridge assembly, comprising:
a body portion including a first row of staple receiving slots and a second row of staple receiving slots, wherein an outer edge comprising a smallest dimension of each staple receiving slot of the first row and second row of staple receiving slots is located farther from a center axis of the staple cartridge assembly than any other point of each staple receiving slot of the first row and second row of staple receiving slots;
wherein the outer edge of each staple receiving slot of the first row of staple receiving slots are a first distance from the center axis of the staple cartridge assembly;
wherein the outer edge of each staple receiving slot of the second row of staple receiving slots are a second distance, different from the first distance, from the center axis of the staple cartridge assembly;
wherein a difference between the first distance and the second distance is less than a largest dimension of the each of the staple receiving slots; and wherein the second row of staple receiving slots are arranged in a generally radial orientation with respect to the center axis of the staple cartridge assembly such that the largest dimension of each of the staple receiving slots in the second row is along a radial line from the center axis of the staple cartridge assembly.

5. The assembly of claim 4, wherein each slot of the first row and second row of staple receiving slots are configured to receive a surgical staple.

6. The assembly of claim 4, wherein the first row of staple receiving slots are oriented at an angle between 0° and 45° to the radial line from the center axis of the staple cartridge assembly to the outer edge of the first row of staple receiving slots.

7. The assembly of claim 4, wherein the body portion includes a knife between the first row of staple receiving slots and the center axis of the staple cartridge assembly.

* * * * *